(12) United States Patent
Gauthier et al.

(10) Patent No.: US 10,315,049 B2
(45) Date of Patent: Jun. 11, 2019

(54) SYSTEM AND METHOD FOR MONITORING STRUCTURAL MOVEMENTS THROUGHOUT RADIATION THERAPY

(71) Applicant: Elekta Ltd., Montreal (CA)

(72) Inventors: Jean-François Gauthier, Montreal (CA); Pierre-Olivier Beaudoin, Montreal (CA); Marc-André Lalonde, MontRoyal (CA); Daniel Lodu, Stittsville (CA); Rui Lopes, Brossard (CA); Martin Emile Lachaine, Montreal (CA)

(73) Assignee: Elekta LTD., Montreal (CA)

( * ) Notice: Subject to any disclaimer, the term of this patent is extended or adjusted under 35 U.S.C. 154(b) by 307 days.

(21) Appl. No.: 14/884,441

(22) Filed: Oct. 15, 2015

(65) Prior Publication Data

US 2017/0106208 A1    Apr. 20, 2017

(51) Int. Cl.
*A61N 5/10* (2006.01)

(52) U.S. Cl.
CPC ......... *A61N 5/1037* (2013.01); *A61N 5/1039* (2013.01); *A61N 5/1049* (2013.01); *A61N 5/107* (2013.01); *A61N 5/1067* (2013.01); *A61N 2005/1051* (2013.01); *A61N 2005/1052* (2013.01); *A61N 2005/1055* (2013.01); *A61N 2005/1058* (2013.01); *A61N 2005/1059* (2013.01); *A61N 2005/1061* (2013.01); *A61N 2005/1074* (2013.01); *A61N 2005/1091* (2013.01)

(58) Field of Classification Search
CPC .... A61N 5/103; A61N 5/1037; A61N 5/1038; A61N 5/1039; A61N 5/1048; A61N 5/1064; A61N 5/1069; A61N 5/107; A61B 6/08; A61B 6/527

See application file for complete search history.

(56) References Cited

U.S. PATENT DOCUMENTS 8,130,907 B2    3/2012  Maurer, Jr. et al.
8,155,729 B1    4/2012  Hsieh et al.
(Continued)

FOREIGN PATENT DOCUMENTS

EP          3362148 A1      8/2018
WO     WO 2013-107472      7/2013
WO     WO-2017064669 A1    4/2017

OTHER PUBLICATIONS

Mayyas et al., Evaluation of Multiple Image-Based Modalities for Image-Guided Radiation Therapy (IGRT) of Prostate Carcinoma: A Prospective Study, Medical Physics 40, 041707 (2013).
(Continued)

*Primary Examiner* — Carrie R Dorna
(74) *Attorney, Agent, or Firm* — Schwegman Lundberg & Woessner, P.A.; Sanjay Agrawal (57) ABSTRACT

A computer-implemented method, a system or a non-transitory computer-readable medium of doing the same, for monitoring movement of anatomical features throughout a radiation treatment session. The method may include monitoring the movement of the anatomical features with a first modality. The method may further include obtaining positional information of the anatomical features with a second modality over a finite acquisition time. The method may also include providing an indication of a clinically relevant movement associated with the anatomical features during the finite acquisition time based on the monitored movement from the first modality.

23 Claims, 5 Drawing Sheets

(56) References Cited

U.S. PATENT DOCUMENTS

2010/0067660 A1* 3/2010 Maurer, Jr. .............. A61B 6/00
378/95
2011/0286642 A1 11/2011 Nord et al.
2012/0035462 A1* 2/2012 Maurer, Jr. .......... A61B 6/5247
600/411
2015/0010126 A1 1/2015 Rotondo et al.

OTHER PUBLICATIONS

Barney et al., Image-Guided Radiotherapy (IGRT) for Prostate Cancer Comparing KV Imaging of Fiducial Markers With Cone Beam Computed Tomography (CBCT), Int. J. Radiation Oncology Biol. Phys., vol. 80, No. 1, pp. 301-305, (2011).
Batter et al., Imaging and Alignment for Image-Guided Radiation Therapy, J Clin. Oncol. 25: 931-937 (2007).
PCT International Search Report in PCT/IB2016/056179 dated Jan. 10, 2017 (4 pages).
"European Application Serial No. 16855044.0, Response filed Dec. 11, 2018 to Office Action dated Jun. 1, 2018", 16 pgs.
"International Application Serial No. PCT/IB2016/056179, International Preliminary Report on Patentability dated Apr. 26, 2018", 6 pgs.
"International Application Serial No. PCT/IB2016/056179, Written Opinion dated Jan. 10, 2017", 4 pgs.
"European Application Serial No. 16855044.0, Extended European Search Report dated Mar. 28, 2019", 5 pgs.

* cited by examiner

SYSTEM AND METHOD FOR MONITORING STRUCTURAL MOVEMENTS THROUGHOUT RADIATION THERAPY

TECHNICAL FIELD

The present invention relates to systems and methods for radiation therapy treatment, and more specifically relates to systems and methods for monitoring structural movements throughout a radiation therapy treatment session.

BACKGROUND

Radiotherapy is used to treat cancers and other ailments in mammalian (e.g., human and animal) tissue. In a radiation therapy treatment session, a high-energy beam is applied from an external source towards a patient to produce a collimated beam of radiation directed to a target site of a patient. The placement and dose of the radiation beam must be accurately controlled to ensure the patient receives the prescribed radiation, and the placement of the beam should be such that it minimizes damage to the surrounding healthy tissue, often called the organ(s) at risk (OARs). One way to improve the accuracy of the beam placement is by the acquisition of planning images, where one or more image is acquired with the patient in the intended treatment position. CT is often the most used primary image, but can complemented with secondary datasets such as MRI, positron emission tomography (PET), ultrasound, single photon emission computerized tomography (SPECT), or other medical imaging modalities which can be registered or fused to the primary dataset to aid with anatomical visualization.

In some cases, 4D planning images can be acquired. 4D techniques have been developed to account for respiratory motion, assuming that respiration is reproducible from cycle to cycle (which is not always the case). The respiratory cycle is sub-divided into bins, for example 10-12 of equal spacing, and an image is produced for every bin by consolidating image information over many imaging cycles. Techniques for this process have been applied to 4D-CT, 4D-MRI, 4D-PET, 4D-ultrasound, and other modalities. Although these techniques are useful for targets that are primarily influenced by respiratory motion, they do not take into account larger variations of patient anatomy over time. Nor are they relevant to organs where other motion processes dominate such as digestive processes, peristalsis, bladder filling, etc.

Physicians can use the planning images to identify and contour a target (e.g., a diseased organ or a tumor) as well as OARs. Contouring can be performed manually, semi-automatically, or automatically. A treatment contour, often referred to as a planned target volume (PTV), is created which includes the target contour plus sufficient margins to account for microscopic disease as well as treatment uncertainties. A radiation dose is prescribed, and a treatment plan is created that optimally delivers the prescribed dose to the PTV while minimizing dose to the OARs and other normal tissues. The treatment plan can be generated manually by a user, or automatically using an optimization technique.

A treatment course is developed to deliver the prescription dose over a number of fractions, each fraction delivered in a different session. For example, 30-40 fractions are typical but 5 or even 1 fraction can be used, and fractions are often delivered once or in some cases twice per weekday. In some cases, the radiation treatment plan can change throughout the course to focus more dose in some areas.

In each fraction, the patient is set up on the patient support accessory (often a "couch") of the linear accelerator and repositioned as closely as possible to their position in the planning images. Unfortunately, this is an impossible task to carry out accurately in practice, since the patient is not a rigid object and the anatomy can move. Fraction-to-fraction motions are often referred to as interfractional motion, while motion occurring during a fraction itself is often referred to as intrafractional motion. Image guided radiotherapy (IGRT) attempts to solve the problem of interfractional motion, which is in many cases the larger of the two types of motion. As opposed to planning images, which can be acquired on any diagnostic scanner, IGRT images must be acquired directly in the treatment room, while the patient is in treatment position. Technologies for IGRT imaging that have been developed are cone-beam CT (CBCT), ultrasound, MRI, portal imaging, CT-on-rails, on-board kV imaging, and others have been either proposed or in development. In some cases, anatomical contrast is low in IGRT images, and fiducial markers are implanted in the patient to help with visibility of the target. Some technologies have been developed that do not use imaging at all, but rely on the imageless detection of the position of active fiducials, for example by implanting radiofrequency (RF) beacons. This is generally still referred to as IGRT, even though strictly speaking, images are not obtained. For generality, we will refer to 'images' as to include positional information of fiducials, or any data collected about the patient's interfractional state, such as target or OAR positions, rotations or deformations, blood pressure, heart rate, weight, deformation, etc.

IGRT refers to not only the collection of image information, but also how to compensate for interfractional state. IGRT images are first compared to the planning images to find changes. A full deformable change over the whole patient anatomy can be found, but it is standard to focus on global shift and/or rotations that match the images as closely as possible. For example, only the shift and rotation of the target itself can be considered, or in some cases bony anatomy or an OAR, or combinations thereof. Once the shifts, rotations and/or deformations have been calculated, the treatment plan is modified to account for these changes. In many cases a complete re-plan is not practical, so the couch is simply shifted to re-align the patient as closely as possible. In other cases, full or partial re-plans are carried out. The IGRT workflow is often used to refer to the entire process of imaging, calculating a correction, and physically carrying out the correction, prior to irradiating the patient.

Each IGRT modality has its advantages and disadvantages. For example, CBCT or stereoscopic kV x-rays are often used because they are x-ray based and thus similar in nature to planning CT images, and can be integrated directly into the linear accelerator. Depending on the target site, fiducials are often inserted into the target with these modalities to enhance visibility. 3D ultrasound has also been used for IGRT, and MRI imaging has more recently been introduced by integrating the MRI into the radiation treatment room.

IGRT compensates for interfractional motions, rather than intrafractional motions. In some cases where respiratory motion dominates, 4D phase-binned IGRT techniques can be used, such as 4D-CBCT. These techniques do not consider other components of motion, and are not applicable to organs such as the prostate, GYN, breast or head and neck where other intrafractional processes dominate. Furthermore, it is often desirable to track the target directly at each point in time during the treatment, and compensate for the tracked motions on the fly. The problem is that some image-based IGRT techniques, such as CBCT or MRI, have a finite acquisition time that is overly long to track the target sufficiently fast. For example, CBCT often takes 1 minute, and MRI imaging often takes 1-3 minutes for a full 3D scan. For this reason, real-time imaging modalities have been developed for target tracking.

We refer to the term target tracking to mean measuring changes in the patient's state quickly enough to accurately represent the motion—for example, at an interval smaller than the respiratory cycle if the target undergoes respiratory motion, or small compared to the probability that a target will move substantially out of alignment between imaging samples. It is also anticipated that other aspect of the patient's state other than the target itself can be tracked, such as OARs, heart rate, etc.

Real-time imaging modalities may use the same underlying imaging technology as IGRT modalities with implementation differences to increase speed, or they may use different imaging technologies altogether. For example, the kV imager used to generate CBCT images in real time can be used during the treatment itself, but only to give projectional information; the missing information must be deduced using an intelligent algorithm. MRI imagers can be configured to 1D navigators, 2D planes, or coarser 3D images, to increase imaging speed. Ultrasound imaging and RF beacons can be directly used to track the target in real time. Surface markers, surface cameras, ECG, EEG can give partial information which can be used to help estimate the target position.

In many cases, it is useful to use different modalities for IGRT target tracking, in some cases using the same underlying imaging technology, and in other cases, different technologies. IGRT has the luxury of not being necessarily real-time, and so the time budget can be used to generate richer 3D information, which is not acceptable for target tracking. IGRT typically operates under the assumption that the target is sufficiently static. However, practically the structure of interest might move significantly during the IGRT acquisition. In that case, the positional information obtained during the IGRT stage can no longer be accurately used by the target tracking stage. For example, a prostate patient may cough move, pass gas, or have significant bladder filling such that the position of his prostate may change during the transition between IGRT and target tracking modalities.

Therefore, there is a need for implementing different modalities for IGRT and target tracking that does not assume that no motion occurs during IGRT and during the transition between modalities.

SUMMARY

Certain embodiments of the present disclosure relate to a computer-implemented method for monitoring movement of anatomical features throughout a radiation treatment session. The method may include monitoring the movement of the anatomical features with a first modality. The method may further include obtaining positional information of the anatomical features with a second modality over a finite acquisition time. The method may also include providing an indication of a clinically relevant movement associated with the anatomical features during the finite acquisition time based on the monitored movement from the first modality.

Certain embodiments of the present disclosure relate to a system for monitoring movement of anatomical features throughout a radiation treatment session. The system may include a processor configured to monitor the movement of the anatomical features with a first modality, obtain positional information of the anatomical features with a second modality over a finite acquisition time, and detect a clinically relevant movement associated with the anatomical features during the finite acquisition time based on the monitored movement from the first modality. The system may also include an output device configured to provide an indication if the clinically relevant movement is detected.

Certain embodiments of the present disclosure relate to a non-transitory computer-readable medium having program instructions stored thereon. The program instructions, when executed by a processor may perform a method for monitoring movement of anatomical features throughout a radiation treatment session. The method may include monitoring the movement of the anatomical features with a first modality. The method may further include obtaining positional information of the anatomical features with a second modality over a finite acquisition time. The method may also include providing an indication of a clinically relevant movement associated with the anatomical features during the finite acquisition time based on the monitored movement from the first modality.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the invention, as claimed.

BRIEF DESCRIPTION OF THE DRAWINGS

The accompanying drawings, which constitute a part of this specification, illustrate several embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise Embodiments of the present disclosure may include an image-guided radiotherapy system. The radiotherapy system may include a high-energy beam source and a control center to control radiation application. Typically, radiotherapy is delivered in a series of individual doses on a regular (e.g. daily) basis—usually referred to as "treatment fractions" or just "fractions". To account for changes in the position or shape of an anatomical feature (e.g., an organ, tumor, tumor bed, gland, critical anatomical structure, or other lesion) between fractions, i.e. "inter-fraction motion," positional information based on an image may be acquired immediately prior to treatment and then the current position and/or shape of the anatomical feature is determined. This positional information is then used to adjust the treatment plan as necessary. The positional information may include one or more Computed Tomography (CT) images, CBCT images, x-ray images (e.g., fluoroscopic x-ray image sequences), radiotherapy portal images, stereo pairs of portal images, stereo pairs of x-ray images, Magnetic Resonance Imaging (MRI) images, Positron Emission Tomography (PET) images, Single-Photon Emission Computed Tomography (SPECT) images, ultrasound images, or other suitable medical images. In some embodiments, the positional information may include a surface representation from a camera, positions of markers on a patient's external surface, or positions of beacons implanted within the patient. High-resolution positional information, such as 3D soft tissue images, may take a certain amount of time. Sometimes, during this time period, significant movement may occur that is not reflected in the positional information acquired.

To monitor and detect movement of the patient during a fraction (referred to as "intra-fraction motion"), target tracking may be performed during the fraction. Real-time images may be preferred for intra-fraction monitoring, where the definition of "real-time" depends on the necessity; it must be very fast, <500 ms and ideally <50 ms for respiratory targets such as the lung, but can be relaxed to 2 seconds or even in some cases up to 30 seconds for slower moving targets such as the prostate. For example, two-dimensional (2D) ultrasound or MRI images, as well as time-efficient three-dimensional (3D) ultrasound or MRI images, may be used to track real-time intra-fractional motion during radiotherapy, as these images may be acquired in real-time and provide real-time information as to organ motion, while not exposing the patient to additional radiation during the monitoring process. Other imaging methods, such as kilovolt planar imaging of fiducial markers and RF beacons can also be used. Surface markers, surface cameras, EEG, and ECG may also be used along with algorithms to estimate the target position from the real-time data.

Consistent with the present disclosure, in order to monitor possible structural movements during the period when the positional information is acquired by the first modality, the second modality may be extended to monitor the movements during that period or at least a portion of that period. The period that the first modality and the second modality overlap is referred as "a transition period," or "an overlapping period." However, the two detection systems for the two modalities normally may not communicate. Therefore, this disclosure provides systems and methods to monitor structural movements during the transition period.

Consistent with this disclosure, a modality refers to an imaging device and an imaging protocol, in some cases with an additional computational scheme, to measure the state of a patient such as the position of a target or OAR, the shape of a target or OAR, deformations of the patient's anatomy, a heart rate, the respiratory phase, a displacement of the patient's chest or abdomen, or any other aspect of the patient that can change either interfractionally or intrafractionally. In some cases two different imaging modalities may use MRI as the imaging device, but have different imaging protocols such as 3D vs 2D, or ultrasound as the imaging device, but have different imaging protocols such as transabdominal and transperineal. In other cases two different imaging modalities can use different imaging devices altogether, such as CBCT and ultrasound.

Consistent with some embodiments, before a radiation therapy session starts, a non-real time modality may be performed to obtain images of a patient, or a target anatomical region of the patient. During the radiation therapy treatment session, the real-time modality may be used to perform real-time monitoring of the target anatomical region. Consistent with some embodiments, a transition period may be used during which both imaging modalities are on. By having both imaging modalities turned on, the disclosed systems and methods may monitor the movement of the structures within the target anatomical region during the transition period. As a result, a correct mapping may be established between the images obtained using the two imaging modalities since the modalities over during the transaction period. The non-real time modality may subsequently be turned off leaving only the real-time modality on, if no clinically relevant movement is detected during the transition period, and thus completing the transition. A clinically relevant movement is defined as a motion that will sufficiently alter the dose delivery to the patient beyond what the physician deems acceptable, and can be defined in some embodiments as a maximum allowable distance defined by the physicians or the treatment margins used for the particular patient.

The following description relates to an example embodiment where CBCT is the exemplary non real-time modality and ultrasound is the exemplary real-time modality. However, it is contemplated that other combinations of imaging modalities may be used. For example, the non real-time imaging modality may be any of CT, CBCT, 3D or 4D MRI, PET, SPECT, kV planar x-ray images of fiducial markers, etc. Real-time imaging modality may be ultrasound imaging, 2D MRI, CT, kV planar x-ray images of fiducial markers, electromagnetic imaging, RF beacons, surface imaging and combinations thereof.

Figure 1:
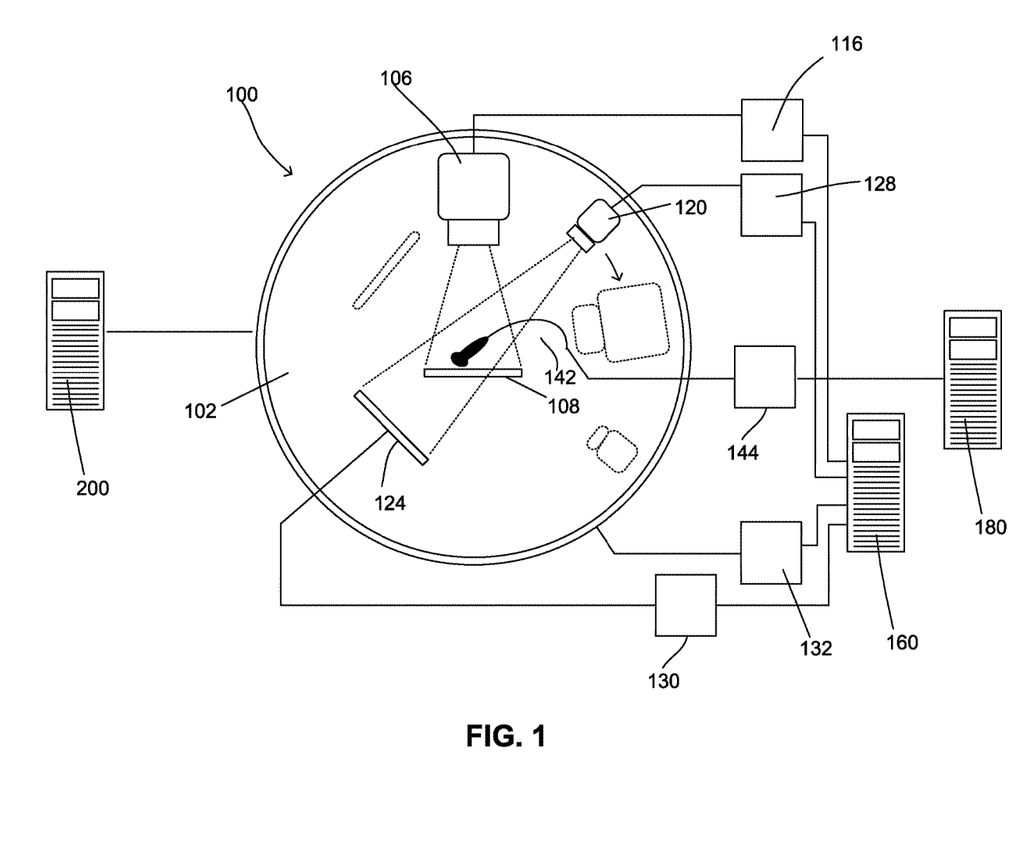
FIG. 1 illustrates an exemplary multi-modality image-guided radiotherapy system, according to some embodiments of the present disclosure.

FIG. 1 illustrates an exemplary multi-modality image-guided radiotherapy system 100, according to some embodiments of the present disclosure. Multi-modality image-guided radiotherapy system 100 may include a radiotherapy treatment delivery system having, among other things, a linear accelerator (not shown), a gantry 102, a radiation source 106 connected to the linear accelerator, a patient support 108, and a source controller 116, configured to deliver high-energy x-ray beams to treat an anatomical region of interest containing, for example, a tumor or microscopic disease.

The gantry 102 may be configured to be rotatable about a central horizontal axis. In some embodiments, a portion of the gantry 102 may be concealed behind a wall or false wall or covers through which the gantry 102 projects. The gantry 102 may carry the radiation source 106. The radiation source 106 may produce a high-energy x-ray beam suitable for therapeutic purposes, and the x-ray beam may be directed toward the central horizontal axis of patient support 108. A beam of electrons from the linear accelerator may be directed onto an x-ray target to produce a beam of high-energy x-rays in the appropriate direction. The radiation beam may be filtered if necessary, such as with a flattening filter. In other embodiments, the radiation beam may be unfiltered. In further embodiments, the radiation beam may be collimated by block collimators and/or multi-leaf collimators to create a therapeutic beam to be applied to the anatomical region of interest. The therapeutic source controller 116 may be configured to control emission of the therapeutic beam from radiation source 106 by modulating one or more of the collimators.

Patient support 108 may be provided, just below the central horizontal axis, for the patient to be laid upon. The patient may be positioned with the anatomical feature located at the point of intersection of the central horizontal axis and the central axis of the therapeutic beam—a point typically referred to as the "isocentre". The patient table 108 may be driven by suitable motors so as to allow adjustment in all six degrees of freedom (three translational and three rotational) in order to position the patient precisely relative to the isocentre. The treatment room may be provided with low-power laser markers, which may converge on the isocentre from a variety of directions, such as the three orthogonal directions in order to assist with positioning the patient.

Radiotherapy system 100 may further include a CBCT imaging system having, among other things, a diagnostic source 120, a flat-panel imager 124, a diagnostic source controller 128, an imager controller 130, and a gantry controller 132, configured to acquire CBCT images of the patient typically before a radiotherapy fraction.

Diagnostic source 120 may be supported on the gantry, in some embodiments located 90 degrees away from the therapeutic source 106. Diagnostic source 120 may be configured to emit a low-energy diagnostic beam of up to about 125 keV in energy towards the isocentre, suitable for producing high-contrast images of human tissue. Both the radiation source 106 and the diagnostic source 120 may be arranged to rotate on the gantry 120, such that the diagnostic source 120 is before the radiation source 106 when rotating.

In some embodiments, as the gantry is rotatable around the patient in order to allow for irradiation from multiple directions, this rotation can be used to allow diagnostic source 120 to develop a CBCT reconstruction. In some embodiments, the diagnostic source 120 is located on the gantry 90 degrees from the therapeutic source, so that with the associated imaging panels for each source opposite the respective source, the items on the gantry are spaced apart and access is maximized.

Flat-panel imager 124 may also be provided on the gantry 102, directly opposite diagnostic source 120 in order to obtain a two-dimensional x-ray image of the patient. Diagnostic source controller 128 may be configured to control and trigger the diagnostic beam. Imager controller 130 may trigger flat-panel imager 124 and read the image together with the gantry angle and pairs this image and angle data together. Radiotherapy system 100 may further include a gantry controller 132 configured to direct the motors to rotate the gantry 102 as necessary. In some embodiments, radiation source 106 and diagnostic source 120 may be combined into one source unit, and the source controller 116 and diagnostic source controller 128 may also be combined.

In some embodiments, radiotherapy system 100 may be integrated with an MRI scanner. In other embodiments, it can generate stereoscopic images mounted in the room. In other embodiments, the system may be non-isotropic and the gantry can be a robotic platform that can irradiation from any non-coplanar angle. Particles such as electrons, protons, or others can be used to irradiate the patient instead of x-rays.

Consistent with some embodiments, radiotherapy system 100 may further include an ultrasound imaging system having, among other components, an ultrasound probe 142 and an ultrasound controller 144, configured to acquire real-time ultrasound images of the patient typically during a radiotherapy fraction.

In some embodiments, ultrasound probe 142 may be two-dimensional probe that may be moved by a motor (not shown) in three-dimensions. The two-dimensional probe may be mounted inside a housing (not shown) and be able to sweep at different angles within the housing, controlled by the motor. In some embodiments, tracking markers may be affixed to the probe handle such that the position of the probe may be detected by a tracking device, e.g., an infrared optical camera. In the disclosed embodiments, ultrasound probe 142 may be any type of ultrasound probe suitable for acquiring two-dimensional or three-dimensional ultrasound images.

Ultrasound controller 144 may be configured to control the motion of ultrasound probe 142. Because the motorized sweeping probe is essentially a two-dimensional probe that moves according to a particular degree of freedom inside the housing, its position within the housing can be quantified in terms of a parameter X. The parameter X can be controlled by ultrasound controller 144 through an interface to the motor. For example, ultrasound controller 144 may instruct the motor to move the two-dimensional probe to a particular location within the housing such that a two-dimensional frame can be acquired at a fixed position X. In other cases, ultrasound controller 142 may instruct the motor to continuously move probe within the housing, facilitating the acquisition of images while continuously changing X.

Radiotherapy system 100 may further include one or more computers in communication with the controllers, including source controller 116, diagnostic source controller 128, imager controller 132, gantry controller 134, and ultrasound controller 144. It is contemplated that the control functions may be arranged differently, such as by further subdividing different functions and/or by amalgamating functions. In some embodiments, therapeutic source controller 116, diagnostic source controller 128, imager controller 132, and gantry controller 134 may be connected to one computer 160 and ultrasound controller 144 may be connected to a separate computer 180. In some embodiments, computer 160 and computer 180 may not automatically communicate with each other. It is contemplated that various known architecturally configurations may be implemented for the controllers.

Computer 160 may be configured to receive and process the 2D images acquired by the flat-panel imager 124. Each 2D image may be stored by computer 160 together with the rotation angle at which it was obtained, derived from gantry controller 134. Computer 160 may process the 2D images to reconstruct a 3D CBCT image. Based on the 2D images or the 3D image, computer 160 may detect positioning error and adjust the collimator settings of a multi-leaf collimator that will be needed when the therapeutic beam is emitted from that rotation angle. Computer 160 may also provide an output that prompts adjustment of the position of patient table 108 or the position of the patient before beginning the radiotherapy fraction. Computer 160 may display the 2D and/or 3D images to an operator.

Computer 180 may be configured to receive and process the ultrasound images acquired by ultrasound probe 142. For example, computer 180 may reconstruct a 3D ultrasound image from images frames obtained through the sweep process. The 3D ultrasound image may be analyzed to detect motion of certain anatomical features. Computer 180 may display the 2D and/or 3D ultrasound images to an operator, so that the operator may monitor the intrafractional motions on a screen.

Radiotherapy system 100 may further include a modality transition controller 200 configured to monitor structural movements during the transition period. For example, modality transition controller 200 may be configured to monitor movements using ultrasound imaging during the CBCT imaging. Modality transition controller 200 may be implemented as a separate controller or as a part of computer 160 or computer 180.

In some embodiments, the ultrasound imaging system and the CBCT imaging system may be turned on before the fraction begins and modality transition controller 200 may be notified. The CBCT imaging system may be turned on before, simultaneously with, or after the ultrasound imaging system is turned on, provided there is a predetermined overlapping time period that both imaging systems are on and performing imaging scans. Modality transition controller 200 may monitor motions of the anatomical feature, such a prostate or a tumor tissue inside an organ, during the overlapping time period. Modality transition controller 200 may be programmed with certain criteria to determine if the motion is clinically relevant. For example, a motion is clinically relevant if the anatomical feature moves out of a predetermined area that is to be treated by the radiotherapy treatment.

If a clinically relevant motion is detected by modality transition controller 200 during the overlapping period, the controller 200 may provide an output to the operator prompting the operator to stop the ongoing CBCT scan and re-initiate it. If the CBCT scan is re-initiated, a new overlapping period begins, and the modality transition controller 200 may continue to monitor clinically relevant motions. If no clinically relevant motion is detected by the modality transition controller 200 by the time it receives a notification that the CBCT scan has been completed, the modality transition controller 200 may determine that the entire overlapping time period is clinically-equivalent (e.g., the anatomical features in the region are clinically static), and consider that the two imaging modalities agree during the period. Accordingly, the modality transition controller 200 may allow the fraction to begin with the ultrasound imaging system as the monitoring mechanism.

Figure 2:
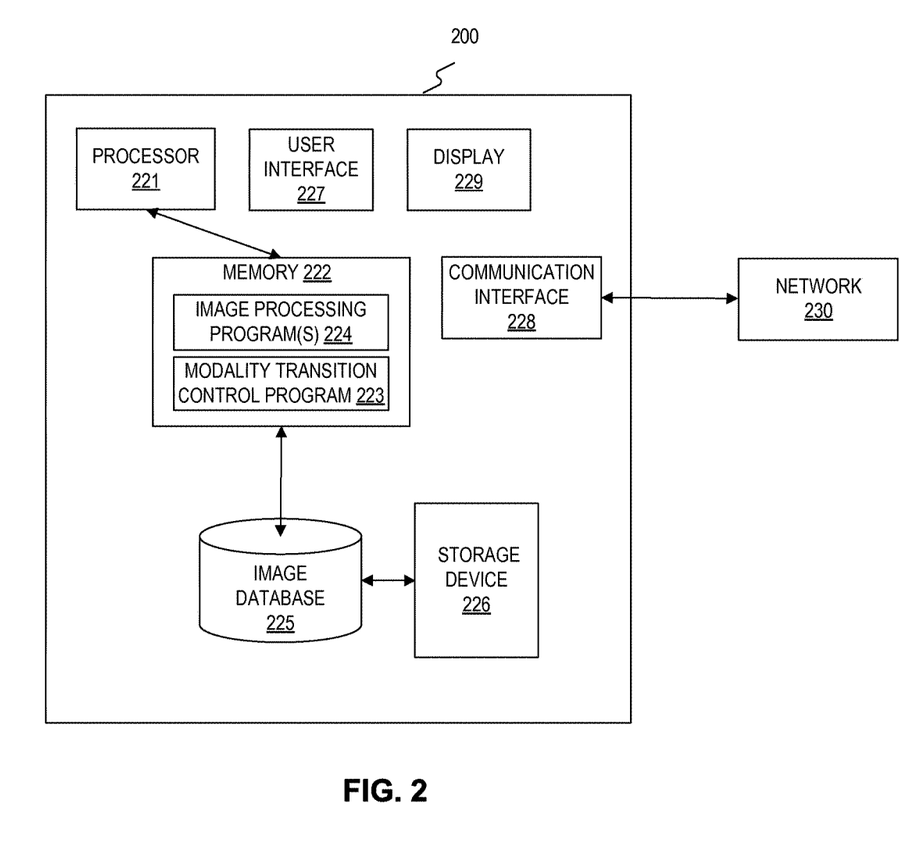
FIG. 2 is a block diagram of an exemplary modality transition controller used in the multi-modality image-guided radiotherapy system of FIG. 1, according to some embodiments of the present disclosure.

FIG. 2 is a block diagram of an exemplary modality transition controller 200 used in the multi-modality image-guided radiotherapy system of FIG. 1, according to some embodiments of the present disclosure. As shown in FIG. 2, modality transition controller 200 may include a processor 221, a memory 222, an image database 225, a storage device 226, a user interface 227, a communication interface 228, and a display 229. It is contemplated that the modality transition controller 200 may include more or less components, or that certain components may be combined.

Processor 221 may be a processing device, include one or more general-purpose processing devices such as a microprocessor, central processing unit (CPU), graphics processing unit (GPU), an accelerated processing unit (APU), or the like. More particularly, processor 221 may be a complex instruction set computing (CISC) microprocessor, reduced instruction set computing (RISC) microprocessor, very long instruction Word (VLIW) microprocessor, a processor implementing other instruction sets, or processors implementing a combination of instruction sets. Processor 221 may also be one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, processor 221 may be a special-purpose processor, rather than a general-purpose processor. Processor 221 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. Processor 112 may also include graphical processing units such as a GPU from the GeForce®, Quadro®, Tesla® family manufactured by Nvidia™, GMA, Iris™ family manufactured by Intel™, or the Radeon™ family manufactured by AMD™. Processor 221 may also include accelerated processing units such as the Desktop A-4(6,8) Series manufactured by AMD™, the Xeon Phi™ family manufactured by Intel™. The disclosed embodiments may include any type of processor(s) otherwise configured to meet the computing demands of identifying, analyzing, maintaining, generating, and/or providing large amounts of imaging data or manipulating such imaging data to localize and track a target or to manipulate any other type of data consistent with the disclosed embodiments. In addition, the term "processor" may include more than one processor, for example, a multi-core design or a plurality of processors each having a multi-core design.

Processor 221 may be communicatively coupled to memory 222 and configured to execute the computer executable instructions stored thereon. Memory 222 may include a read-only memory (ROM), a flash memory, a random access memory (RAM), a static memory, etc. In some embodiments, memory 222 may store computer executable instructions, such as one or more modality transition control program 223 or image processing programs 224, as well as data used or generated while executing the computer programs, such as image data. Processor 221 may execute modality transition control program 223 to monitor structural movements during the transition period between the CBCT imaging system and the ultrasound imaging system as described and shown with respect to FIG. 1.

Processor 221 may also send/receive image data from memory 222, and execute image processing programs 224 to perform image processing tasks including image reconstruction, image registration, image segmentation, feature recognition, image rendering, etc. For example, processor 221 may perform image segmentation and recognition to identify the anatomic feature from the CBCT images or the ultrasound images. Processor 221 may then track the motion of the anatomic feature and determine if the motion is clinically relevant. In some embodiments, processor 221 may also perform image registration to register the medical images acquired with different imaging modalities (e.g., register CBCT images with the ultrasound images).

Modality transition controller 200 may optionally include an image database 225. One skilled in the art would appreciate that image database 225 may include a plurality of devices located either in a central or distributed manner. Processor 221 may communicate with image database 225 to read images into memory 222 or store segmented images from memory 222 to medical image data 225. In some embodiments, image database 225 may include medical images captured by the CBCT imaging system and the ultrasound imaging system in FIG. 1.

Storage device 226 may be an additional storage available to store data associated with processing tasks performed by processor 221. In some embodiments, storage device 226 may include a non-transitory machine-readable storage medium. While the machine-readable storage medium in an embodiment may be a single medium, the term "non-transitory machine-readable storage medium" should be taken to include a single medium or multiple media (e.g., a centralized or distributed database, and/or associated caches and servers) that store the one or more sets of computer executable instructions or data. The term "non-transitory machine-readable storage medium" shall also be taken to include any medium that is capable of storing or encoding a set of instructions for execution by the machine and that cause the machine to perform any one or more of the methodologies of the present disclosure. The term "non-transitory machine-readable storage medium" shall accordingly be taken to include, but not be limited to, solid-state memories, optical and magnetic media.

User interface 227 may be configured to allow data to be received and/or transmitted by modality transition controller 200. User interface 227 may include one or more digital and/or analog communication devices that allow modality transition controller 200 to communicate with user. For example, user interface 227 may include a keyboard, a mouse, a microphone, a clicker, and/or a touch screen for the operator of radiotherapy system 100 to provide input to modality transition controller 200. In certain embodiments, the user interface 227 may include a tablet type device, a cell-phone, or any wireless device.

Communication interface 228 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 228 may include one or more digital and/or analog communication devices that permit modality transition controller 200 to communicate with other machines and devices, such as remotely located components, via a network 230. The network 230 may provide the functionality of a local area network (LAN), a wireless network, a cloud computing environment (e.g., software as a service, platform as a service, infrastructure as a service, etc.), a client-server, a wide area network (WAN), and the like.

Display 229 may be any display device that suitable for displaying information to the user. For example, image display 229 may be an LCD, CRT, or LED display. In some embodiments, display 229 may provide one or more user interface dialogue windows to the user for user to make selections e.g., by pressing on buttons or checking boxes in the windows. In some embodiments, display 229 may be integrated with user interface 227. For example, display 229 may be a touch screen display that can receive user inputs provided by user's fingers.

In some embodiments, display 229 may also display one or more of the medical images acquired by the CBCT imaging system and the ultrasound imaging system of FIG. 1. For example, display 229 may show the medical images segmented by processor 221, with or without the anatomic feature highlighted for the user. In some embodiments, display 229 may overlay the pre-determined criteria of clinically relevant movement on top of the medical images, so that the user can see whether and when the motion becomes clinically relevant. In some embodiments, display 229 may also display registered images acquired by different imaging modalities, such as registered CBCT and ultrasound images.

Figure 3:
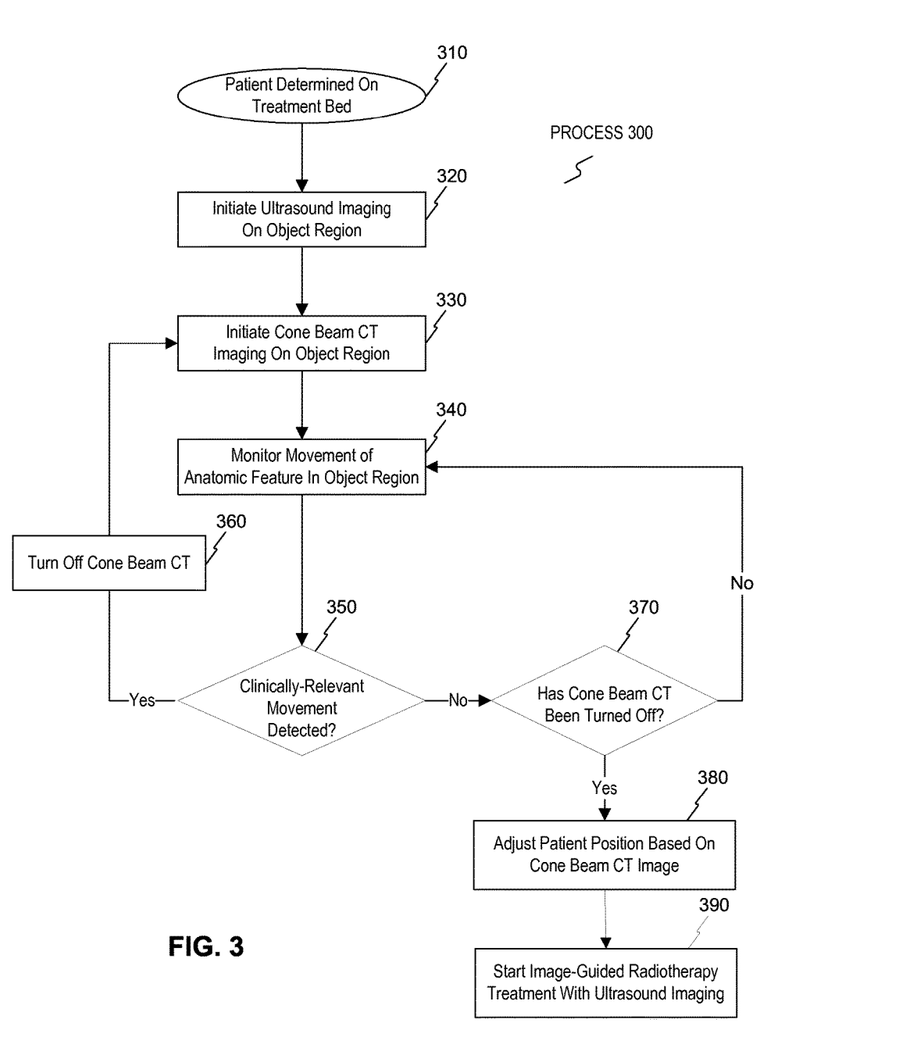
FIG. 3 is a flowchart of an exemplary process for monitoring structural movements throughout a radiation therapy treatment session, according to some embodiments of the present disclosure.

FIG. 3 is a flowchart of an exemplary process 300 for monitoring structural movements throughout a radiation therapy treatment session, according to some embodiments of the present disclosure.

At step 310, process 300 may begin when the system determines the patient is properly positioned on patient table 108. Alternatively, process 300 may be initiated by the user. In certain embodiments, the position of the patient may be fixed through the use of a restraining device.

At step 320, monitoring a target region on the patient may be initiated using a first imaging modality. The first imaging modality may be a real-time imaging modality where images can be acquired and reconstructed in real-time (e.g., 2D or 3D ultrasound imaging, etc.). For example, an operator may initiate ultrasound imaging to monitor the patient or a target anatomical region of the patient through computer 180. Ultrasound imaging may provide real-time tracking of the position and/or shape of anatomical features in the anatomical region. After the ultrasound imaging system is turned on, the operator may notify modality transition controller 200 that the ultrasound imaging is initiated. In some embodiments, the notification may be provided automatically by computer 180.

At step 330, an imaging scan of the target region may be initiated using a second imaging modality. The second imaging modality may be a real-time or a non real-time imaging modality (e.g., CBCT, 3D MRI, etc.). For example, an operator may initiate a CBCT scan through computer 160, and notify modality transition controller 200 that the CBCT system is turned on. The CBCT scan usually provides high-resolution 3D images, based on with position errors can be detected. Patient position and/or position of the collimator associated with the radiation source may be adjusted based on the CBCT images prior to delivery of the radiotherapy treatment. In some embodiments, the notification may be provided automatically by computer 160. Although in FIG. 3, step 320 is shown as before step 330, it is contemplated that step 330 may occur simultaneously with or after step 320.

At step 340, certain anatomical features (e.g., an organ such as prostate, breast, lungs, or a tumor(s) in any organ) may be monitored to determine if a clinically relevant movement of the anatomical features has occurred. In some embodiments, step 340 may use the imaging data obtained in the preceding steps. The images may be segmented either manually by an operator or automatically by processor 221. For example, images may be segmented into regions corresponding to static background and different moving objects. The motion of the anatomical features may be detected based on the segmented images. For example, the position and/or shape of the anatomical features may be determined based on the segmented images, and compared to that in a reference image captured prior to or at the beginning of step 330. In some embodiments, processor 221 may also implement other motion detection and recognition methods, such as correlation-based matching methods, feature-based methods, optical flow techniques, change-based moving object detection methods, and any other suitable motion detection or estimation methods used for video processing.

At step 350, processor 221 may determine if a clinically relevant amount of movement is detected. Processor 221 may further compare the movement, determined as described above, with predetermined criteria corresponding to a clinically relevant movement. In some embodiments, the predetermined criteria may define spatial boundaries for the movement, such that the movement becomes clinically relevant if it exceeds the spatial boundaries. In some embodiments, the predetermined criteria may include threshold values corresponding to one or more of translation, rotation, scaling, and deformation of the anatomical feature. If parameters of the anatomical feature exceed the respective threshold value, the movement becomes clinically relevant.

If a clinically relevant movement is detected (step 350: yes), process 300 may proceed to step 360. In step 360, modality transition controller 200 may provide an indication of clinically relevant movement to the operator, e.g., via display 229. For example, display 229 may show that the anatomical feature has moved out of a boundary set by the predetermined criteria. Criteria depend on the target and treatment margins, but for prostate treatments exceptional criteria can be 3 mm or 5 mm, or that the prostate moves outside of the PTV defined in the treatment plan. Alternatively or additionally, the indication may be provided by a dialogue window on display 229, or by an audible signal. The operator, upon receiving the indication, may turn off CBCT via computer 160, and process 300 may return to step 330 to re-initiate a new CBCT scan. In some other embodiments, the indication may be provided automatically to computer 160, which may automatically turn off the CBCT. In some embodiments, the operator may note the clinically relevant movement but does not stop and reinitiate the CBCT scan.

If no clinically relevant movement is detected (step 350: no), process 300 may proceed to step 370, where it is determined whether the second imaging modality (e.g., CBCT) is still on. In some embodiments, modality transition controller 200 may receive a notification when the CBCT scan is completed and the CBCT system is turned off. The notification may be provided by the operator or automatically by computer 160.

If the CBCT scan is ongoing (step 370: no), it is still within the transition period. Accordingly, process 300 may go back to step 340 to monitor the movement of the anatomical features. If the CBCT scan has successfully completed its scan (step 370: yes), the process 300 may continue to 380. During step 370, the processor 221 may determine that the overlapping time period is clinically equivalent and thus the two imaging modalities agree. Consistent with this disclosure, the two modalities may be considered to agree if a common physical position can be referenced in the coordinate associated with each respective system (e.g., a mapping can be established between a position in the CBCT image and a position in the ultrasound image).

In some embodiments, after step 370, computer 160 may notify the operator that position of the patient or patient table 108 may need to be adjusted to compensate for any interfractional motion detected through the CBCT scan. For example, patient table 108 may need to be shifted or rotated. The CBCT scan may also be used to modify other aspects of the radiation therapy treatment plan, such as morphing apertures, rotating apertures, shifting apertures, and a dosimetric re-plan. In step 380, the adjustment may be performed by the operator, or automatically through controls of patient table 108. Once the adjustment is completed, process 300 may proceed to step 390 to start the radiotherapy treatment. The first imaging modality may remain on to monitor any intrafractional movements.

Figure 4:
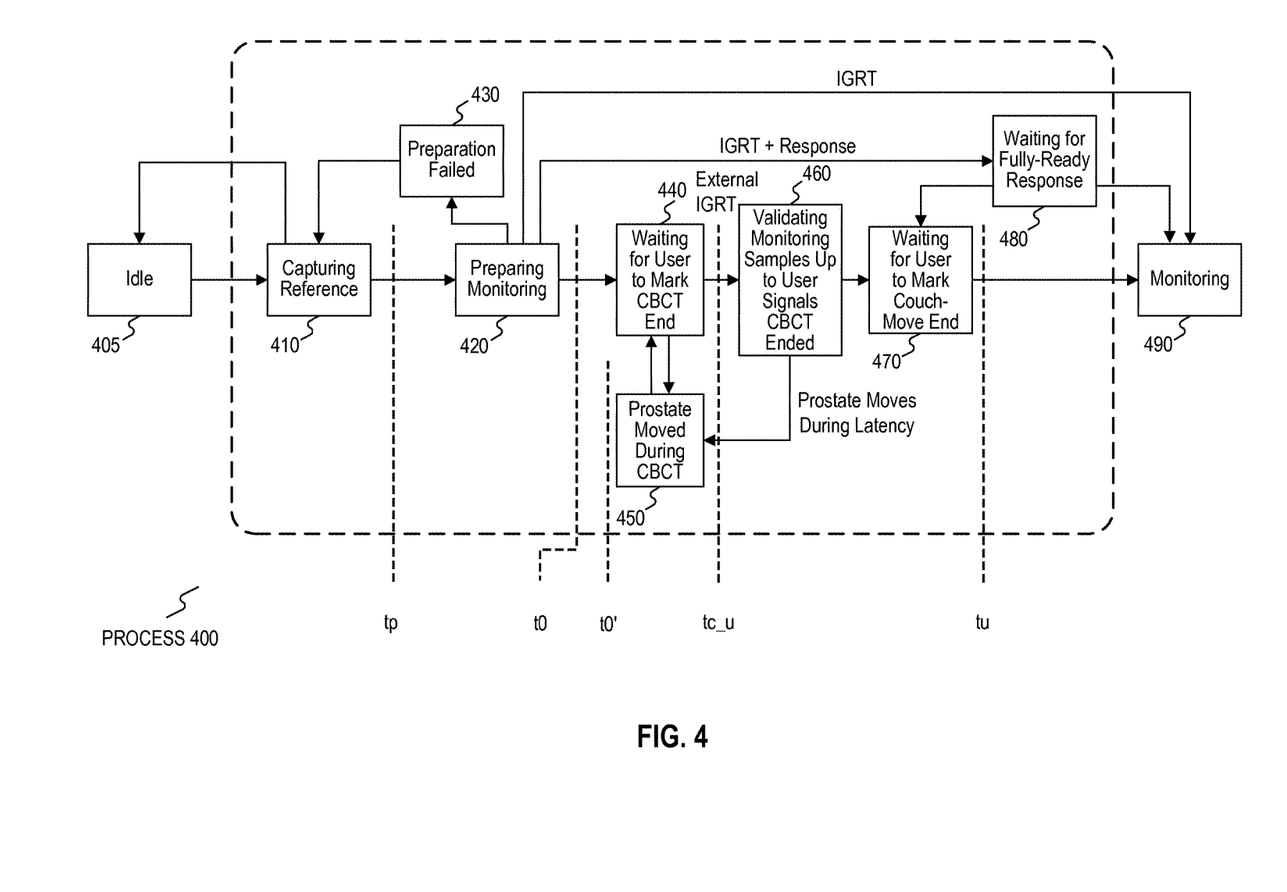
FIG. 4 shows an exemplary process performed by the modality transition controller of FIG. 2, according to some embodiments of the present disclosure.
Figure 5:
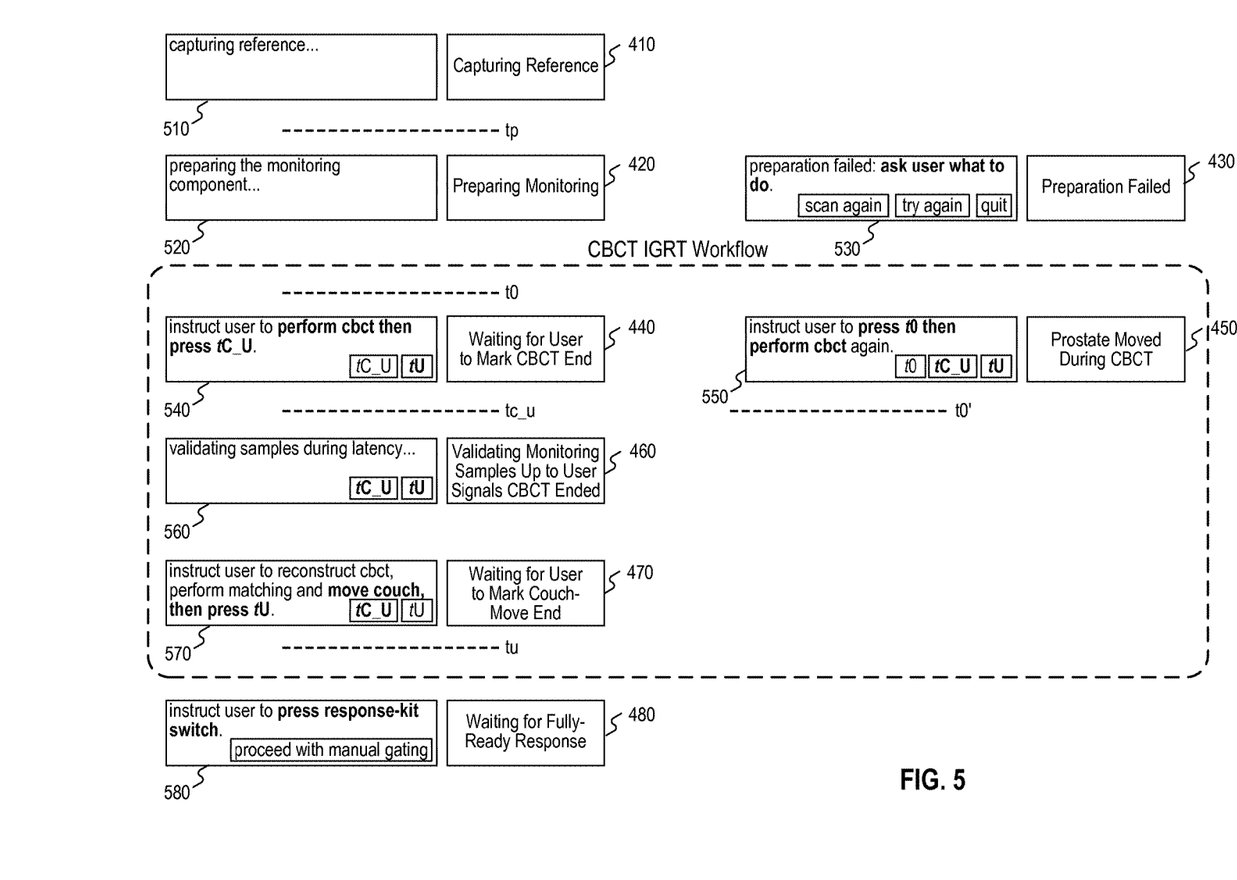
FIG. 5 illustrates exemplary user interface dialogues provided by the modality transition controller of FIG. 2, according to some embodiments of the present disclosure.

FIG. 4 shows an exemplary process 400 performed by modality transition controller 200 of FIG. 2, according to some embodiments of the present disclosure. FIG. 5 illustrates exemplary user interface dialogues 510-580 provided by modality transition controller of FIG. 2, corresponding to process 400 of FIG. 4, according to some embodiments of the present disclosure. Thus, FIGS. 4 and 5 need to be referred to below.

In step 405, the system may be idle. During this time, the patient may be positioned on patient table 108. In step 410, modality transition controller may capture a reference image of the patient using, e.g., ultrasound imaging. A UI dialogue 510 may be displayed on display 229, showing "capturing reference . . . " After capturing the reference image, the system may go back to idle (step 405), or proceed to the preparation phase.

From time point tp, modality transition controller 200 may prepare for monitoring of the radiotherapy session in step 420. Accordingly, a UI dialogue 520 may be displayed on display 229, showing "preparing the monitoring component . . . " In one embodiment, as part of step 420, modality transition controller 200 may check if the ultrasound system is turned on. If preparation fails (step 430), a UI dialogue 530 may present on display 229 that asks the operator to select among three options: scan again, try again, or quit. If the operator selects "scan again" on UI dialogue 530, process 400 may go back to step 420 to capture another reference scan.

At time point t0, the first monitoring sample may be received by modality transition controller 200. In step 440, modality transition controller 200 may instruct the operator to perform a CBCT scan and then wait for a notification that the CBCT scan is completed. A UI dialogue 540 may be present on display 229 that instructs the user to perform a CBCT scan and to then press a button tC_U indicating that the scan is completed. If during the CBCT scan, the anatomical feature (e.g., a prostate) moved and if the modality transition controller 200 determines that the movement is clinically relevant (step 450), a UI dialogue 550 may present on display 229 instructing the user to press t0 and then perform a CBCT scan again at time point t0'. If the clinically relevant movement occurs during the period that both CBCT and ultrasound imaging are on, the images acquired by these two imaging systems cannot be properly registered with each other. Therefore, the overlapping period needs to be restarted by reinitiating the CBCT scan.

In step 460, modality transition controller 200 may continuously validate monitoring samples, such as ultrasound images acquired by the ultrasound imaging system in FIG. 1, until the user press the tC_U button on a UI dialogue 560. If during step 460, a clinically relevant movement is detected by modality transition controller 200, process 400 may go to step 450, and have the user re-initiate a new CBCT scan. If no clinically relevant movement is detected when the user press the tC_U button, a UI dialogue 570 may be present on display 229 to instruct the user to reconstruct the CBCT image, perform matching and move patient table if necessary to adjust patient position. In step 470, modality transition controller 200 may wait for the user to provide a notification that the adjustment has been completed at time point tU. The user may press the tU button on UI dialogue 570.

In step 480, modality transition controller 200 may wait for a fully-ready response from the radiotherapy delivery system and the ultrasound imaging system. A UI dialogue 580 may be present on display 229 to instruct the user to press "proceed with manual gating" to provide the fully-ready response. Once the button on UI dialogue 580 is pressed, process 400 may proceed with radiotherapy and ultrasound monitoring in step 490.

Although FIG. 4 and FIG. 5 are disclosed as requiring user to manually provide notifications related to the imaging systems, as well as requiring user to initiate the imaging scans, it is contemplated that the disclosed embodiments are only exemplary. In some other embodiments, at least some of these notifications may be received automatically from computer 160 and/or computer 180. In some embodiments, the imaging scans such as the CBCT scan or ultrasound monitoring may be initiated automatically with a control signal sent from modality transition controller 200 to computer 160 and/or computer 180.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present invention also relates to a system for performing the operations herein. This system may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A computer-implemented method for controlling a radiotherapy device by monitoring movement of one or more anatomical features during a radiation treatment session performed by the radiotherapy device, the method comprising:

monitoring the movement of the one or more anatomical features with a first modality by using a first imaging device associated with the first modality for a first finite acquisition time;

obtaining first positional information of the one or more anatomical features with the first modality during the first finite acquisition time;

monitoring the movement of the one or more anatomical features with a second modality by using a second imaging device associated with the second modality for a second finite acquisition time, wherein the second finite acquisition time overlaps with at least a portion of the first finite acquisition time;

obtaining second positional information of the one or more anatomical features with the second modality during the second finite acquisition time;

while the second imaging device performs a scan, comparing a parameter of a first image obtained, during the second finite acquisition time, using the first imaging device with a parameter of a second image obtained, during the second finite acquisition time, using the second imaging device;

controlling completion of the scan performed by the second imaging device in response to detecting movement based on the comparison of the parameters of the first and second images; and providing, based on the comparison of the parameters of the first and second images, an indication of the movement based on the obtained first positional information of the one or more anatomical features and based on the second positional information obtained during the second finite acquisition time, wherein the indication of the movement is used to control the radiotherapy device during the radiation treatment session.

2. The method according to claim 1, further including modifying a treatment plan of the radiation treatment based on the positional information obtained using the second modality.

3. The method according to claim 2, wherein modifying includes at least one of a patient table shift, a patient table rotation, morphing apertures, rotating apertures, shifting apertures, and a dosimetric re-plan.

4. The method according to claim 1, further including detecting the movement when the movement exceeds pre-determined criteria, wherein controlling completion of the scan comprises initiating a new scan to be performed using the second imaging device when the movement exceeds the pre-determined criteria, and wherein controlling completion of the scan comprises completing the scan using the second imaging device when the movement fails to exceed the pre-determined criteria.

5. The method according to claim 4, wherein the pre-determined criteria includes threshold values corresponding to one or more of translation, rotation, scaling, and deformation of the anatomical feature in the object region.

6. The method according to claim 1, further comprising obtaining new positional information of the one or more anatomical features with the second modality over the second finite acquisition time if the movement is detected during the second finite acquisition time.

7. The method according to claim 1, wherein the first modality is a real-time modality and the second modality is a non real-time modality, and wherein controlling completion of the scan comprises turning off the second imaging device in response to detecting the movement.

8. The method according to claim 1, wherein the first modality is one of ultrasound imaging, two-dimensional Magnetic Resonance Imaging (MRI), X-ray imaging, kilovolt planar imaging of fiducial makers, monitoring cameras, and RF beacons.

9. The method according to claim 1, wherein the second modality is one of Computed Tomography (CT), Cone-Beam Computed Tomography (CBCT), Magnetic Resonance Imaging (MRI), Positron Emission Tomography (PET), single-photo emission computed tomography (SPECT), kilovolt planar imaging of fiducial markers, ultrasound imaging, monitoring cameras, and RF beacons.

10. The method according to claim 1, the first modality is ultrasound imaging and the second modality is Cone-Beam Computed Tomography (CBCT).

11. The method according to claim 1, wherein the start or the end of the second finite acquisition time is approximated by receiving a notification corresponding to the start or the end of the use of the second modality.

12. The method according to claim 1 further comprising registering the first image obtained, during the second finite acquisition time, using the first imaging device and the second image obtained, during the second finite acquisition time, using the second imaging device.

13. A system for controlling a radiotherapy device by monitoring movement of one or more anatomical features during a radiation treatment session performed by the radiotherapy device, the system comprising:
a processor configured to:
monitor the movement of the one or more anatomical features with a first modality by using a first imaging device associated with the first modality for a first finite acquisition time;
obtain first positional information of the one or more anatomical features with the first modality during the first finite acquisition time;
monitor the movement of the one or more anatomical features with a second modality by using a second imaging device associated with the second modality for a second finite acquisition time, wherein the second finite acquisition time overlaps with at least a portion of the first finite acquisition time;
obtain second positional information of the one or more anatomical features with the second modality over the second finite acquisition time;
while the second imaging device performs a scan, compare a parameter of a first image obtained, during the second finite acquisition time, using the first imaging device with a parameter of a second image obtained, during the second finite acquisition time, using the second imaging device;
detect, based on the comparison of the parameters of the first and second images, movement based on the obtained first positional information of the one or more anatomical features and based on the second positional information obtained during the second finite acquisition time, wherein the detection of the movement is used to control the radiotherapy device during the radiation treatment session; and
control completion of the scan performed by the second imaging device in response to detecting the movement.

14. The system according to claim 13, wherein the movement is detected when the movement exceeds pre-determined criteria, wherein controlling completion of the scan comprises initiating a new scan to be performed using the second imaging device when the movement exceeds the pre-determined criteria, and wherein controlling completion of the scan comprises completing the scan using the second imaging device when the movement fails to exceed the pre-determined criteria.

15. The system according to claim 13, wherein the first modality is a real-time modality and the second modality is a non real-time modality, and wherein controlling completion of the scan comprises turning off the second imaging device in response to detecting the movement.

16. The system according to claim 13, the first modality is ultrasound imaging and the second modality is Cone-Beam Computed Tomography (CBCT).

17. The system according to claim 13, further including a user interface configured to receive a notification corresponding to the start or the end of the use of the second modality, and wherein the start or end of the second finite acquisition period is approximated based on the notification.

18. The system according to claim 13, wherein the processor is further configured to register the first image obtained, during the second finite acquisition time, using the first imaging device and the second image obtained, during the second finite acquisition time, using the second imaging device.

19. A non-transitory computer-readable medium having program instructions stored thereon, the program instructions, when executed by a processor, performing a method for controlling a radiotherapy device by monitoring movement of one or more anatomical features during a radiation treatment session performed by the radiotherapy device, the method comprising:
monitoring the movement of the one or more anatomical features with a first modality by using a first imaging device associated with the first modality for a first finite acquisition time;

obtaining first positional information of the one or more anatomical features with the first modality during the first finite acquisition time;

monitoring the movement of the one or more anatomical features with a second modality by using a second imaging device associated with the second modality for a second finite acquisition time, wherein the second finite acquisition time overlaps with at least a portion of the first finite acquisition time;

obtaining second positional information of the one or more anatomical features with the second modality over the second finite acquisition time; and while the second imaging device performs a scan, comparing a parameter of a first image obtained, during the second finite acquisition time, using the first imaging device with a parameter of a second image obtained, during the second finite acquisition time, using the second imaging device;

controlling completion of the scan performed by the second imaging device in response to detecting movement based on the comparison of the parameters of the first and second images; and providing, based on the comparison of the parameters of the first and second images, an indication of the movement based on the obtained first positional information of the one or more anatomical features and based on the second positional information obtained during the second finite acquisition time, wherein the indication of the movement is used to control the radiotherapy device during the radiation treatment session.

20. The non-transitory computer readable medium according to claim 19, wherein the movement is detected when the movement exceeds pre-determined criteria wherein controlling completion of the scan comprises initiating a new scan to be performed using the second imaging device when the movement exceeds the pre-determined criteria, and wherein controlling completion of the scan comprises completing the scan using the second imaging device when the movement fails to exceed the pre-determined criteria.

21. The non-transitory computer readable medium according to claim 19, wherein the first modality is a real-time modality and the second modality is a non real-time modality, and wherein controlling completion of the scan comprises turning off the second imaging device in response to detecting the movement.

22. The non-transitory computer readable medium according to claim 19, wherein the start or the end of the second finite acquisition time is approximated by receiving a notification corresponding to the start or the end of the use of the second modality.

23. The non-transitory computer readable medium according to claim 19 further comprising registering the first image obtained, during the second finite acquisition time, using the first imaging device and the second image obtained, during the second finite acquisition time, using the second imaging device.

* * * * *

UNITED STATES PATENT AND TRADEMARK OFFICE
CERTIFICATE OF CORRECTION

| | | |
|---|---|---|
| PATENT NO. | : 10,315,049 B2 | Page 1 of 1 |
| APPLICATION NO. | : 14/884441 | |
| DATED | : June 11, 2019 | |
| INVENTOR(S) | : Gauthier et al. | |

It is certified that error appears in the above-identified patent and that said Letters Patent is hereby corrected as shown below:

On the Title Page

On page 2, in Column 1, under "Other Publications", Line 5, delete "Batter" and insert --Balter-- therefor In the Claims In Column 20, Line 3, in Claim 20, after "criteria", insert --,--

Signed and Sealed this
Fourteenth Day of April, 2020

Andrei Iancu
*Director of the United States Patent and Trademark Office*